United States Patent [19]

Schwartz

[11] 4,052,667
[45] Oct. 4, 1977

[54] MOISTURE METER CONSTRUCTION

[75] Inventor: Edwin L. Schwartz, Los Angeles, Calif.

[73] Assignee: Rite Autotronics Corporation, Los Angeles, Calif.

[21] Appl. No.: 721,534

[22] Filed: Sept. 8, 1976

[51] Int. Cl.² ............................................. G01R 27/02
[52] U.S. Cl. .................................................. 324/65 P
[58] Field of Search ................. 324/65 P, 65 R, 61 P, 324/61 R, 30 R, 149

[56] References Cited

U.S. PATENT DOCUMENTS

| 3,141,129 | 7/1964 | Dietert | 324/65 R |
| 3,412,325 | 11/1968 | Soderling | 324/65 R |
| 3,794,913 | 2/1974 | Cropper et al. | 324/65 P |

Primary Examiner—Stanley T. Krawczewicz
Attorney, Agent, or Firm—Robert E. Geauque

[57] ABSTRACT

A moisture meter construction in which a conventional meter assembly is mounted within a housing, an access opening into said housing, a tubular member integrally secured to said housing having an opening therethrough with the opening of the tubular member being aligned with the access opening, an annular chamber surrounding the tubular member, a metallic probe assembly tightly fitted within said annular chamber, a tapered plug member surrounding a portion of the metallic probe assembly being snugly located within said annular chamber, the free end of the probe assembly having an electrical insulator placed within the metallic probe member and a dissimilar metal located interiorly of the insulator with the entire probe assembly being tightly sealed.

3 Claims, 3 Drawing Figures

U.S. Patent     Oct. 4, 1977     4,052,667
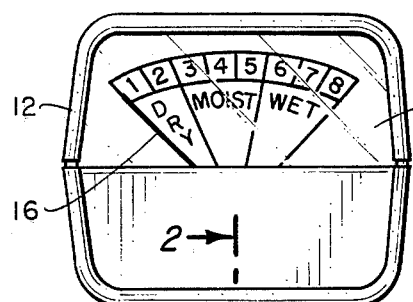
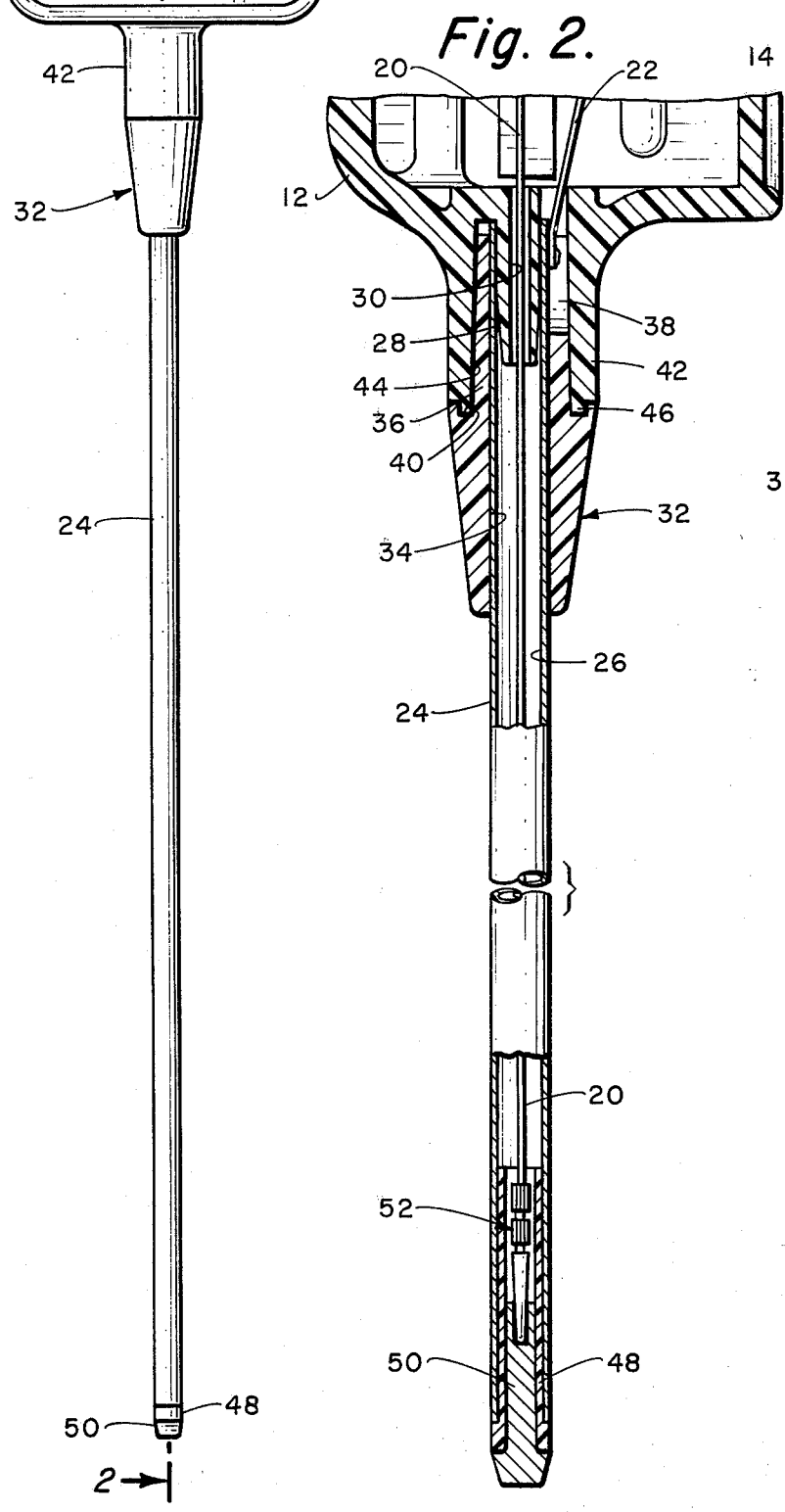
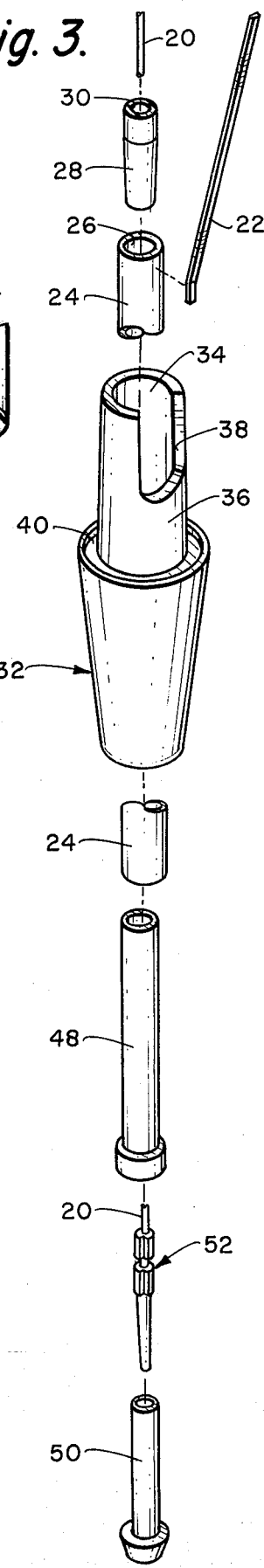

MOISTURE METER CONSTRUCTION

BACKGROUND OF THE INVENTION

The field of this invention relates to electrical meter devices and more particularly to a combination of an electrical meter and connecting probe with the probe to be placed within a flower pot with the probe measuring electrical conductivity within the soil which is indicative of the amount of moisture in the soil and the amount of moisture being read upon an electrical meter.

Electrical meters of the type which use dissimilar metals to measure moisture content is well known. These meters function on the principle of a solid electrolyte battery which uses an ion exchange beimetallic cell. If the two metals are insulated from each other but located in close proximity to one another and moisture is placed between the metals, there will be an ion exchange therebetween. This ion exchange produces a small amount of electrical current. The greater the amount of moisture the greater the electrical current. The smaller the amount of moisture the smaller the electrical current.

Recently, such meters have been constructed to measure the amount of moisture in flower pots. A common problem having to do with the raising of plants is that the plants may be readily over watered or readily under watered. Prior to the use of such moisture meters, the watering of plants was merely guess work. It was only estimated the quantity of moisture located in the bottom of a flower pot.

Recently, such moisture meters has been constructed with a long probe with the probe being insertable to within the flower pot and the probe be located at the bottom thereof. The quantity of moisture located in the bottom of the pot then becomes between the dissimilar metals of the probe and electrical current is conducted therebetween. This electrical current is measured by an electrical coil, which, in turn, causes movement of a pointer. This movement is detected by the face of a meter which by appropriate indicia on the face of the meter gives an indication, by the position of the pointer, as to the amount of moisture contained within the flower pot.

SUMMARY OF THE INVENTION

The structure of this invention is believed to be summarily described within the Abstract Of The Disclosure and reference is to be had thereto.

The primary objective of this invention is to construct a moisture meter which is tightly sealed to prevent moisture from entering within the interior of the meter and corrode or otherwise damage the interior components of the meter.

Another objective of this invention is to design a moisture meter composed of relatively few parts which can be easily assembled, with the overall assembly to be inexpensively to manufacture.

BRIEF DESCRIPTION OF THE DRAWING

FIG. 1 is a front view of a moisture meter of this invention;

FIG. 2 is a cross-sectional view taken along line 2—2 of FIG. 1; and

FIG. 3 is an exploded isometric view of the probe assembly incorporated within the moisture meter of this invention.

DETAILED DESCRIPTION OF THE SHOWN EMBODIMENT

Referring particularly to the drawing, there is shown the moisture meter 10 of this invention which is composed of a meter housing 12 which has an internal chamber 14 for the supporting of appropriate conventional electrical meter apparatus (not shown). The meter apparatus is to include an electrical coil (not shown) which, in turn, is connected to a pointer 16. This pointer 16 is movable across the face 18 of the meter and upon the face 18 is located appropriate indicia to indicate moisture content. Small movements of the needle of the pointer 16 will indicate dry conditions with intermediate movements of the pointer indicating moist conditions and substantial movement of the pointer indicating wet conditions.

One side of the coil (not shown) is attached to electrical conducting wire 20. The other side of the coil is attached to electrical lead 22. Electrical lead 22 is fixedly secured to electrically conductive tubular member 24. This tube 24 is basically cylindrical in shape in cross-section and has an internal chamber 26 therein. Preferable material of construction for the tube 24 is nickel-plated brass.

The inner end of the tube 24 is to be located about tubular extension 28 which is formed integral with the housing 12. There is to be a snug or tight fit between the extension 28 and the tube 24 with the extension 28 located partially within the chamber 26.

Within the tubular extension 28 is located an elongated opening 30 which aligns with the access opening of the housing 12 providing access to within the chamber 14. Also located about the member 24 is a plug 32. This plug 32 has an internal elongated opening 34 through which the member 24 passes. The inner end of the plug 32 includes a smaller diametered tapered section 36. This tapered section 36 includes a cutout section 38 which is to provide access for the electrical lead 22 to be connected to the member 24.

At the inner connection of the section 36 with the main body portion of the plug 32 is an annular recess 40. It is to be noted that the tubular section is tapered outwardly, that is, the portion of the tubular section 36 adjacent the recess 40 is of a slightly greater diameter than the outer portion of the section 36.

Also formed integrally with the housing 12 is an annular extension 42 which surrounds the tubular section 28 but is spaced therefrom forming an annular chamber 44. Normally, the chamber 44 will be of basically cylindrical shape. The material of construction for the housing 12, as well as the plug 32, will be a plastic material and this type of material is capable of a slight amount of resiliency. The section 36 is to be forcibly inserted within the chamber 44 until an annular protuberance 46 cooperates within the recess 40. In this position, because of the tapering of the section 36, the annular extension 42 has been forced slightly outwardly with the resulting of a tight interconnection between the plug 32, the member 24 and the tubular section 28. Because of the inserting of the annular protuberance 46 to within the annular recess 40 as well as the previously mentioned tight interconnection between all of the parts, it is very unlikely that any moisture will be caused to seep into the interior of any portion of the meter 10 of this invention.

Within the free end of the member 24 is snugly retained an insulator 48 constructed out of a plastic or other similar non-electrically conductive material. Partially positioned within a portion of the electrical insulator 48 is a magnesium rivet 50. It is to be noted that there are dissimilar metals of the magnesium rivet 50 and the nickel-plated brass member 24.

The electrically conducting member 20 is fixedly secured by means of a conventional connector apparatus 52 to the rivet 50. It is to be understood that the rivet 50 is tightly positioned within the insulator 48 with the insulator 48 also being tightly positioned within the member 24.

In operation of the device 10 of this invention, electrical current is conducted between the members 50 and 24 across moisture droplets contained therebetween. The amount of moisture available varies directly with the electrical conductivity.

What is claimed is:

1. A moisture meter construction wherein a probe assembly is attached to a housing for the moisture meter, the improvement comprising:
   a tubular extension formed upon said housing having an internal access opening providing access to the interior of the housing;
   a first electrically conductive member tightly mounted upon said tubular section, said first electrically conductive member being tubular and having an elongated chamber therein;
   said housing having an annular extension surrounding said tubular section and being spaced therefrom forming an annular internal chamber;
   a plug member surrounding a portion of said first electrically conductive member with a portion of said plug member to tightly interfit within said internal chamber;
   an insulator located within the outer end of said first electrically conductive member; and
   a second electrically conductive member being tightly mounted within said insulator.

2. The moisture meter apparatus as defined in claim 1 wherein:
   a portion of said plug member located within said internal chamber being tapered so that the cross-sectional diameter of the outermost portion of said portion being of smaller diameter than the innermost section of said portion, whereby as said portion is inserted within said internal chamber there is achieved a progressively tighter interconnection between said portion and said annular extension of said housing and said first metallic member about said tubular extension.

3. The moisture meter apparatus as defined in claim 2 wherein:
   said annular extension having on its outer end thereof an annular raised member, an annular recess formed within said plug member, said annular raised member to interlockingly cooperate within said annular recess forming a tight interconnection therebetween.

* * * * *